(12) United States Patent
Peters et al.

(10) Patent No.: US 7,473,812 B2
(45) Date of Patent: *Jan. 6, 2009

(54) METHOD FOR PRODUCING BUTENE OLIGOMERS AND TERT-BUTYL ETHERS FROM $C_4$ FLOWS CONTAINING ISOBUTENE

(75) Inventors: Udo Peters, Marl (DE); Dieter Reusch, Marl (DE); Andreas Beckmann, Recklinghausen (DE); Dirk Roettger, Recklinghausen (DE); Jochen Praefke, Marl (DE)

(73) Assignee: OXENO Olefinchemie GmbH, Marl (DE)

( * ) Notice: Subject to any disclaimer, the term of this patent is extended or adjusted under 35 U.S.C. 154(b) by 454 days.

This patent is subject to a terminal disclaimer.

(21) Appl. No.: 10/543,148

(22) PCT Filed: Dec. 3, 2003

(86) PCT No.: PCT/EP03/50930

§ 371 (c)(1),
(2), (4) Date: Jul. 25, 2005

(87) PCT Pub. No.: WO2004/065338

PCT Pub. Date: Aug. 5, 2004

(65) Prior Publication Data

US 2006/0122444 A1   Jun. 8, 2006

(30) Foreign Application Priority Data

Jan. 23, 2003 (DE) ................... 103 02 457

(51) Int. Cl.
*C07C 2/06* (2006.01)
*C07C 43/00* (2006.01)
(52) U.S. Cl. ............... 585/326; 585/329; 568/697
(58) Field of Classification Search ........... 585/329, 585/326; 568/697
See application file for complete search history.

(56) References Cited

U.S. PATENT DOCUMENTS

| 5,723,687 | A | * | 3/1998 | Marchionna et al. ........ 568/697 |
| 2004/0054246 | A1 | | 3/2004 | Nierlich et al. |
| 2004/0097773 | A1 | | 5/2004 | Beckmann et al. |

FOREIGN PATENT DOCUMENTS

| DE | 29 44 457 | 5/1981 |
| EP | 0 081 041 | 6/1983 |
| EP | 1 074 534 | 2/2001 |
| EP | 1 199 296 | 4/2002 |
| JP | 60 058932 | 4/1985 |
| WO | 02/064531 | 8/2002 |

OTHER PUBLICATIONS

U.S. Appl. No. 10/519,397, filed Jan. 3, 2005, Obenaus et al.

* cited by examiner

*Primary Examiner*—Thuan Dinh Dang
(74) *Attorney, Agent, or Firm*—Oblon, Spivak, McClelland, Maier & Neustadt, P.C.

(57) ABSTRACT

The invention relates to a process for preparing butene oligomers and tert-butyl ethers from $C_4$ hydrocarbon streams, by converting the isobutene to butene oligomers and tert-butyl ethers and removing them from the $C_4$ streams.

10 Claims, 2 Drawing Sheets

METHOD FOR PRODUCING BUTENE OLIGOMERS AND TERT-BUTYL ETHERS FROM $C_4$ FLOWS CONTAINING ISOBUTENE

The invention relates to a process for preparing butene oligomers and tert-butyl ethers from $C_4$ hydrocarbon streams, by converting the isobutene to butene oligomers, in particular to isobutene oligomers, and tert-butyl ethers and removing them from the $C_4$ streams.

Isobutene, linear butenes and their subsequent products are obtained in large amounts from technical $C_4$ cuts, for example the $C_4$ cut from steam crackers or FCC units. These mixtures consist substantially of butadiene, the monoolefins isobutene, 1-butene and the two 2-butenes and also the saturated hydrocarbons isobutane and n-butane. Owing to the small boiling point differences of the ingredients and their low separating factors, distillative workup is difficult and uneconomic. Linear butenes and other products are therefore usually obtained by a combination of chemical conversions and physical separating operations.

Depending on whether the butenes have a high or low 1-butene content, the $C_4$ cuts are worked up in different ways. The first step which is common to all workup variants is the removal of the majority of the butadiene. If butadiene can be profitably marketed or there is an internal demand, it is removed by extraction or extractive distillation. Otherwise, it is selectively hydrogenated to linear butenes down to a residual concentration of approx. 2000 ppm by mass. In both cases, a hydrocarbon mixture (known as raffinate I or hydrogenated crack-$C_4$) remains which, in addition to the saturated hydrocarbons n-butane and isobutane, comprises the olefins isobutene, 1-butene and 2-butenes (cis and trans).

When the aim is to prepare isobutene and 2-butene or a mixture of linear butenes having a high 2-butene content, preference is given to the following workup sequence: $C_4$ streams which typically contain not more than 1% of butadiene ($C_4$ stream from FCC (fluid catalytic cracker), raffinate I or hydrogenated crack-$C_4$) are hydrogenated and hydroisomerized, i.e. butadiene present is selectively hydrogenated down to a residual content of less than 5 ppm, and 1-butene is at the same time isomerized to 2-butenes. The equilibrium position between 1-butene and the two 2-butenes at 80° C. is approx. 1:17, i.e. far over to the side of the 2-butenes. Owing to the small boiling point differences, it is possible to obtain only a mixture of isobutene, 1-butene and isobutane as the top product, which is worked up in the customary manner, from the hydroisomerization mixture. The bottom product obtained is an isobutene-free mixture which consists of 2-butenes and n-butane. When the hydroisomerization is carried out in a reactive distillation column, virtually 1-butene-free isobutene can be obtained.

When 1-butene is one of the target products, the further procedure may be as follows: isobutene is removed from raffinate I or hydrogenated crack-$C_4$ by chemical conversion. After the removal of the isobutene, a hydrocarbon mixture (raffinate II) remains which comprises the linear butenes and the saturated hydrocarbons isobutane and n-butane. This mixture can be further separated distillatively, for example into isobutane and 1-butene and a mixture of the two 2-butenes and n-butane. 1-Butene can be obtained in high purity from the 1-butenic fraction in further distillation steps and contains only small amounts of isobutene. This is necessary, since 1-butene is used to a large extent as a comonomer in ethylene polymerization, where isobutene impurities are undesired. Typical specifications of 1-butene therefore limit the content of isobutene in the 1-butene to less than 1000 ppm.

The chemical conversion of the isobutene can be carried out in water to give the tert-butyl alcohol (TBA). Owing to the low solubility of water in $C_4$ hydrocarbons, this route is costly and inconvenient and therefore expensive. In addition, it is barely possible to realize complete isobutene removal.

Another possibility is to oligomerize the isobutene and remove the oligomer. A disadvantage is that the complete isobutene removal by oligomerization also converts a large portion of the linear butenes present to co- or homooligomers. A further disadvantage is the partial isomerization of 1-butene to the 2-butenes.

A further possibility for removing isobutene is its reaction with alcohols, for example methanol or ethanol, to give the corresponding tertiary butyl ethers.

The industrially most important process is the reaction of isobutene with methanol to give methyl tert-butyl ether (MTBE) which finds extensive use mainly as a fuel additive.

Owing to the groundwater contamination which has occurred in the USA, an increasingly critical view is taken of the use of tertiary butyl ethers, in particular MTBE, as an octane number improver in gasoline fuels. It cannot be ruled out that the current and future discussions will lead to restriction of the use of tertiary butyl ethers in fuels.

Since the use of butyl ethers as fuel additives will not take up the entire amount of isobutene in the future, there is interest in other methods of removing isobutene from $C_4$ mixtures with chemical conversion. The preparation of oligomers of isobutene and their removal from the remaining $C_4$ mixture is a promising possibility.

EP 0 048 893 describes a process for coproducing isobutene oligomers and alkyl tert-butyl ethers from $C_4$ cuts in a reactor. The catalyst used is an acidic ion exchange resin whose exchange sites are partly occupied by metals of the seventh and eighth transition groups of the Periodic Table of the Elements in elemental form (oxidation state 0). The products and the unconverted $C_4$ hydrocarbons are separated distillatively. In this process, approximately 8% of the linear butenes are lost by oligomerization. The loss of 1-butene is 7%. However, the main disadvantage of this process is that complete isobutene conversion is not achieved, so that the isobutene content in the $C_4$ hydrocarbon fraction removed is too high to obtain on-spec 1-butene therefrom.

U.S. Pat. No. 5,723,687 likewise describes a process for coproduction of isobutene oligomers and MTBE or ETBE by reaction of a $C_4$ cut, for example raffinate I, in the presence of methanol or ethanol over an acidic ion exchange resin in a reactor. The losses of 1-butene are not disclosed. A disadvantage of this process is the low isobutene conversion which, according to the examples, is only between 78 and 94%.

The use of modified ion exchangers for oligomerizing isobutene is disclosed in DE 101 13 381. However, the isobutenic streams used here contain virtually no further unsaturated compounds such as n-butenes.

DE 29 44 457 describes a process for coproducing isobutene oligomers and MTBE from $C_4$ hydrocarbon cuts, for example raffinate I. In a first reaction step, from 50 to 90% of the isobutene is oligomerized over a strongly acidic catalyst. The remaining isobutene is reacted with methanol in a second reaction step to give MTBE. The reaction products and the unconverted $C_4$ hydrocarbons are removed distillatively. This process has the following disadvantages:

a) Over 30% of the linear butenes are lost by oligomerization.
b) The losses of 1-butene by oligomerization and isomerization are more than 33%.

c) The isobutene content in the remaining $C_4$ hydrocarbon mixture is over 0.7%, i.e. highly pure 1-butene having an isobutene content of less than 1000 ppm cannot be prepared from this mixture.

Since the abovementioned processes are unsatisfactory with regard to the 1-butene yield and/or the isobutene content in the $C_4$ hydrocarbon mixture (raffinate II) removed, it is an object of the present invention to develop an improved process.

Figure 1:
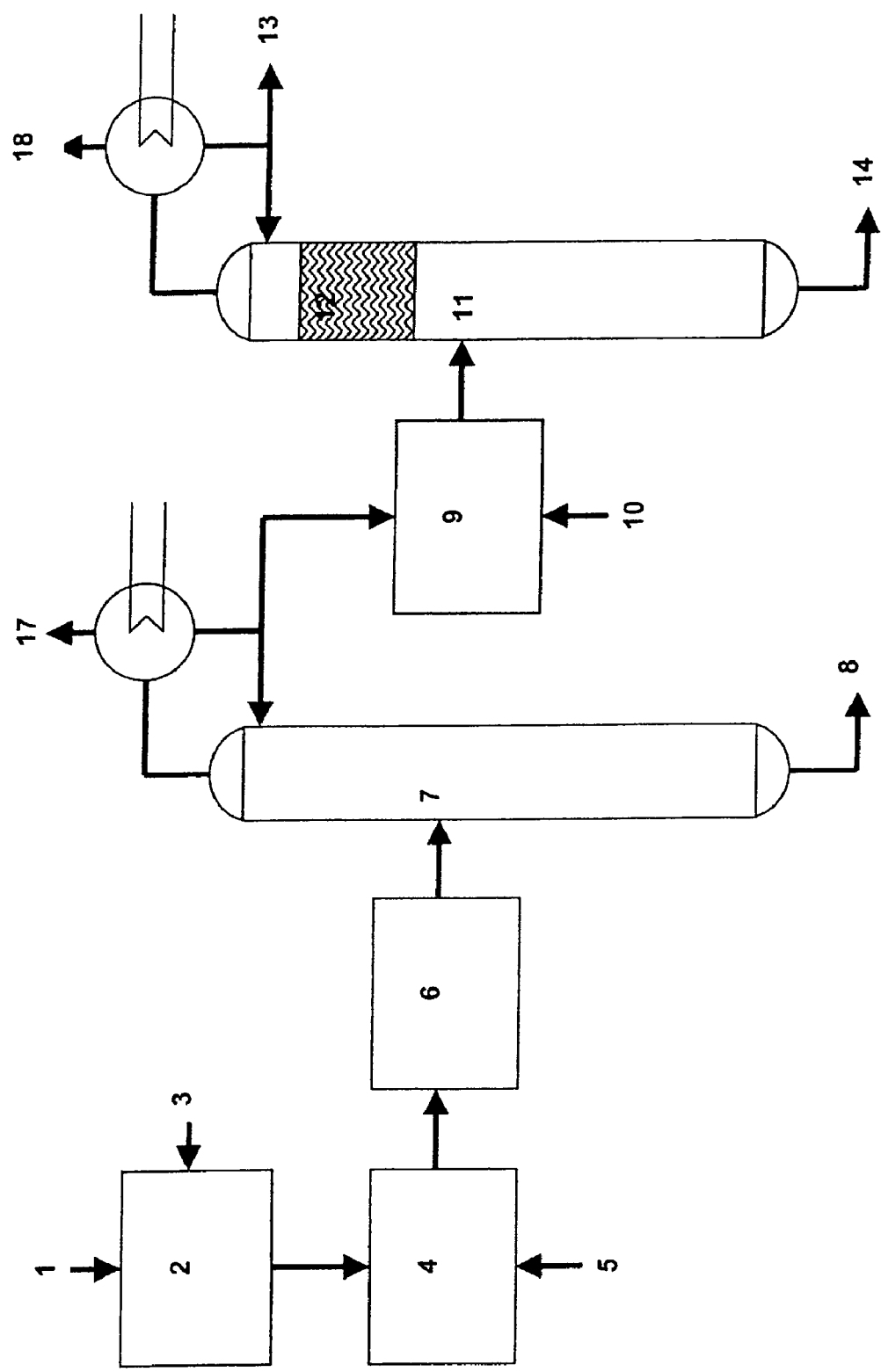
FIG. 1 shows a schematic diagram of an embodiment of the process of the invention.

It has now been found that isobutene can be fully removed from a substantially butadiene-free $C_4$ hydrocarbon stream with only small losses of linear butenes, by oligomerizing a portion of the isobutene in a first reaction step over acidic catalysts whose activity has been modified by the addition of moderators or ion exchange, and removing the remaining isobutene in a second reaction step by reacting with alcohol to give a tert-butyl ether in a reactive distillation column.

In contrast to the existing processes, only a small portion of the 1-butene present in the mixture is lost by isomerization to the 2-butenes.

The present invention therefore provides a process for coproducing butene oligomers and tert-butyl ethers from isobutenic $C_4$ streams by a) partly oligomerizing the isobutenic $C_4$ streams over an acidic catalyst to give butene oligomers and subsequently b) etherifying the remaining isobutene with an alcohol under acidic catalysis to give tert-butyl ethers, which comprises carrying out the etherification under acid catalysis in stage b) in at least two reaction stages, of which at least the last reaction stage is carried out as a reactive distillation.

For the purposes of the present invention, butene oligomers are in particular isobutene oligomers such as di-, tri- or tetramers of isobutene. To a slight extent, these may also comprise cooligomers with or of 1- or 2-butenes.

The butene oligomers prepared according to the invention preferably comprise more than 90% of isobutene oligomers, and the oligomer mixture more preferably has
90-97% of isobutene oligomers
1-8% of iso- and n-butene cooligomers and
0.1-2% of n-butene oligomers.

With the aid of the process according to the invention, it is possible from $C_4$ streams to produce not only the products of value tert-butyl ether and isobutene oligomers, but also isobutene-free residual streams which are suitable for preparing 1-butene. In addition to the unconverted constituents of the $C_4$ feed (in general $C_4$ aliphatics), the isobutene-free residual streams only contain n-butenes, i.e. 1-butene, cis-2-butene and trans-2-butene. It is possible to remove 1-butene from this mixture distillatively (any i-butane removed together with the 1-butene can be removed from 1-butene in a second distillation step). The remaining 2-butenes which may in some cases still contain 1-butene are in turn valuable feedstocks for preparing linear butene oligomers where the presence of isobutene would lead to undesirably high degrees of branching.

Suitable isobutenic $C_4$ streams are, for example, light petroleum fractions from refineries, $C_4$ fractions from crackers (for example steam crackers, hydrocrackers, catalytic crackers), mixtures from Fischer-Tropsch syntheses, mixtures from the dehydrogenation of butanes, mixtures of skeletal isomerization of linear butenes and mixtures resulting from metathesis of olefins. These techniques are described in the literature, cf. K. Weissermel, H. J. Arpe, Industrielle Organische Chemie, Wiley-VCH, 5th edition, 1998, page 23-24; 65-99; 122-124.

Preference is given to using $C_4$ fractions from steam crackers which are primarily operated to produce ethene and propene and in which the raw materials used are, for example, refinery gases, naphtha, gas oil, LPG (liquefied petroleum gas) and NGL (natural gas liquid), or catalytic crackers. Depending on the cracking process, the by-produced $C_4$ cuts contain different amounts of isobutene. Further main constituents are 1,3-butadiene, 1-butene, c-2-butene, t-2-butene, n-butane and i-butane. In the case of $C_4$ fractions from steam crackers, typical isobutene contents in the $C_4$ fraction are from 18 to 35%, and in the case of FCC catalytic crackers are from 10 to 20%.

For the process according to the invention, it is advantageous to remove polyunsaturated hydrocarbons such as 1,3-butadiene from the starting mixture. This can be effected by known processes, for example by extraction, extractive distillation or complex formation (cf. K. Weissermel, H. J. Arpe, Industrielle Organische Chemie, Wiley-VCH, 5th edition, 1998, page 119-121).

An alternative to the removal of the polyunsaturated hydrocarbons is a selective chemical conversion. For example, 1,3-butadiene can be selectively hydrogenated to linear butenes, as described, for example, in EP 0 523 482. The 1,3-butadiene can also be at least partly removed by selective conversions of the 1,3-butadiene, for example dimerization to cyclooctadiene, trimerization to cyclododecadiene, polymerization or telomerization reactions. In all cases in which a crack-$C_4$ cut has been used as the raw material, a hydrocarbon mixture (raffinate I or hydrogenated crack-$C_4$ (HCC$_4$)) remains which comprises mainly the saturated hydrocarbons n-butane and isobutane, and the olefins isobutene, 1-butene and 2-butenes.

In the process according to the invention, preference is given to catalytically hydrogenating the polyunsaturated hydrocarbons contained in the isobutenic $C_4$ streams before the oligomerization in stage a). The polyunsaturated hydrocarbons are mainly 1,3-butadiene; 1,2-butadiene, butenyne and 1-butyne, if at all, are present in a distinctly smaller amount. The hydrogenation can be effected in a one- or multistage hydrogenation process in the liquid phase over a palladium catalyst. To reduce the 1,3-butadiene content to below 1000 ppm, a moderator which increases the selectivity of the palladium catalyst is added in the last stage of the hydrogenation. The moderator used is preferably carbon monoxide which is added in a proportion of from 0.05 to 100 ppm by weight. The content of polyunsaturated hydrocarbons in the feed to this stage should preferably be below 1%, preferably below 0.5%. In the literature, this type of selective hydrogenation of remaining 1,3-butadiene is known as the SHP (selective hydrogenation process) (cf. EP 0 081 041; Erdöl, Kohle, Erdgas, Petrochem. 1986, 39, 73).

When amounts greater than 1% of polyunsaturated hydrocarbons such as 1,3-butadiene are present in the isobutenic $C_4$ streams, they are converted in preceding hydrogenations. These hydrogenations are preferably carried out in the liquid phase over a palladium catalyst. Depending on the content of unsaturated hydrocarbons, the hydrogenation can be carried out in a plurality of stages. For converting crack-$C_4$ from a steam cracker having a typical 1,3-butadiene content of 38-45%, a two-stage conversion of the hydrogenation has proven useful. In this case, individual or all stages can be provided with partial product recycling. In this way, 1,3-butadiene concentrations in the effluent of less than 1% are obtainable, so that a further conversion can be effected in an SHP stage.

The hydrocarbon mixtures comprising isobutene and linear butenes used in the process according to the invention preferably have the following compositions:

TABLE 1

Typical compositions of hydrocarbon mixtures which are used in the process according to the invention

| Component | Steam cracker | | Steam cracker | | Catalytic cracker | |
|---|---|---|---|---|---|---|
| | $HCC_4$ | $HCC_4$/SHP | Raff.I | Raff.I/SHP | $CC_4$ | $CC_4$/SHP |
| isobutane [% by wt.] | 1-4.5 | 1-4.5 | 1.5-8 | 1.5-8 | 37 | 37 |
| n-butane [% by wt.] | 5-8 | 5-8 | 6-15 | 6-15 | 13 | 13 |
| t-butene [% by wt.] | 18-21 | 18-21 | 7-10 | 7-10 | 12 | 12 |
| 1-butene [% by wt.] | 35-45 | 35-45 | 15-35 | 15-35 | 12 | 12 |
| isobutene [% by wt.] | 22-28 | 22-28 | 33-50 | 33-50 | 15 | 15 |
| c-butene [% by wt.] | 5-9 | 5-9 | 4-8 | 4-8 | 11 | 11 |
| 1,3-butadiene [ppm] | 500-5000 | 0-50 | 50-8000 | 0-50 | <10 000 | 0-50 |

Explanation:
$HCC_4$: typical of a $C_4$ mixture which is obtained from the crack-$C_4$ of a steam cracker (high severity) after the hydrogenation of the 1,3-butadiene without additional moderation of the catalyst.
$HCC_4$/SHP: $HCC_4$ composition in which 1,3-butadiene residues have been further reduced in an SHP.
Raff.I (raffinate I): typical of a $C_4$ mixture which is obtained from the crack-$C_4$ of a steam cracker (high severity) after the removal of the 1,3-butadiene, for example by an NMP extractive rectification.
Raff.I/SHP: Raff.I composition in which residues of 1,3-butadiene have been further reduced in an SHP.
$CC_4$: typical composition of a crack-$C_4$ which is obtained from a catalytic cracker.
$CC_4$/SHP: $CC_4$ composition in which 1,3-butadiene residues have been further reduced in an SHP.

Among others, raffinate I or $HCC_4$ is an isobutenic hydrocarbon mixture used with preference for the purposes of this invention. However, since plants for working up $C_4$ hydrocarbons are generally constructed as a chain (combination of a plurality of plants), it is possible that the raffinate I or $HCC_4$ passes through one or more other process stages before entry into the process according to the invention. In this way, an individually adapted overall plan for workup can be realized in each case with the appropriate product portfolio.

Typical process stages which may precede the process according to the invention are water scrubbing, purification on adsorbers, selective hydrogenation, TBA synthesis, drying and distillation.

Water Scrubbing

Water scrubbing can be used to fully or partly remove hydrophilic components from the hydrocarbon mixture comprising isobutene and linear butenes, for example nitrogen components. Examples of nitrogen components are acetonitrile or N-methylpyrrolidone (which may result, for example, from a 1,3-butadiene extractive distillation). Oxygen compounds (for example acetone from FCC crackers) can also be partly removed by water scrubbing. The isobutenic hydrocarbon stream is saturated with water after water scrubbing. In order to avoid biphasicity in the reactor in the subsequent process steps, the reaction temperature there should be approximately 10° C. above the temperature of the water scrubbing.

Adsorbers

Adsorbers are used in order to remove impurities. This may be advantageous, for example, when noble metal catalysts are used in one of the process steps. Often, nitrogen or sulfur compounds are removed by upstream adsorbers. Examples of adsorbers are aluminas, molecular sieves, zeolites, activated carbon, clay earths impregnated with metals. Adsorbers are sold by various firms, for example Alcoa (Selexsorb®).

Selective Hydrogenation (SHP)

Polyunsaturated compounds still present in small amounts, in particular 1,3-butadiene, are further depleted by further selective hydrogenation (cf. EP 0 081 041; Erdöl, Kohle, Erdgas, Petrochem. 1986, 39, 73). The SHP can be operated either as part of a butadiene hydrogenation (see above), or as an independent process step.

TRA Synthesis

Portions of the isobutene can be reacted with water to give tert-butanol (TBA). Processes for preparing TBA from isobutenic hydrocarbon mixtures form part of the prior art (cf., for example, Erdöl, Erdgas, Kohle, 1987, 103, 486). TBA is, for example, used as a solvent, but is also used for preparing highly pure isobutene by dissociation to give isobutene and water.

Drying

Any water present in the isobutenic hydrocarbon mixture which may, for example, stem from the water scrubbing or TBA synthesis can be removed by known processes for drying. Suitable processes are, for example, the distillative removal of water as an azeotrope. Often, an azeotrope with $C_4$ hydrocarbons present can be utilized or azeotroping agents are added.

The drying of the hydrocarbon mixture may be advantageous for various reasons, for example reduction of the formation of alcohols (mainly tert-butyl alcohol) in the oligomerization/etherification, prevention of (uncontrolled) water moderation in the butene oligomerization, avoidance of technical problems by separation of water or ice at low temperatures (for example intermediate storage).

Distillation

Distillation steps can be used, for example, to remove impurities (for example low boilers such as $C_3$ hydrocarbons, high boilers such as $C_5$ hydrocarbons) or to obtain fractions having different isobutene concentrations. This can be effected directly with the raffinate I or the $HCC_4$, or after passing through one or more other process stages. Direct distillation of the raffinate I or of the $HCC_4$ makes possible, for example, a separation into a 2-butenes- and n-butane-depleted, isobutene-richer fraction.

Inventive Oligomerization of Stage a

The partial oligomerization in stage a) of the isobutene can in principle be carried out homogeneously, i.e. using catalysts soluble in the reaction mixture, or heterogeneously, i.e. using catalysts insoluble in the reaction mixture. The disadvantage of the homogeneous processes is that the catalyst leaves the reactor with the reaction products and unconverted reactants, from which it has to be removed, worked up and disposed of or recycled.

Owing to the cost and inconvenience of the separation, the partial oligomerization of the isobutene is preferably carried out over solid heterogeneous catalysts which are additionally often arranged in a fixed bed, so that a costly and inconvenient catalyst removal is unnecessary.

Useful solid catalysts are acidic materials which are insoluble in the reactant/product mixture. Most of these catalysts belong to one of the following groups:

a) mineral acids (e.g. sulfuric acid or phosphoric acid) on a support material (e.g. alumina or silica)
b) zeolites or other aluminosilicates, undoped or doped with other metals, in particular with transition metals,
c) acidic ion exchange resins Owing to the high selectivity for the formation of isobutene oligomers and owing to the minor formation of by-products, preference is given to using acidic ion exchange resins as catalysts.

Suitable ion exchange resins are, for example, those which are prepared by sulfonating phenol/aldehyde condensates or cooligomers of aromatic vinyl compounds. Examples of aromatic vinyl compounds for preparing the cooligomers are styrene, vinyltoluene, vinylnaphthalene, vinylethylbenzene, methylstyrene, vinylchlorobenzene, vinylxylene and divinylbenzene. In particular, the cooligomers which result from reaction of styrene with divinylbenzene are used as a precursor for the preparation of ion exchange resins having sulfo groups. The properties of these resins, in particular specific surface area, porosity, stability, swelling or shrinkage and exchange capacity, can be varied via the preparation process. The resins can be prepared in a gellike, macroporous or spongelike form. Strongly acidic resins of the styrene-divinylbenzene type are sold, inter alia, under the following tradenames: CT 151 from Purolite, Amberlyst 15, Amberlyst 35, Amberlite IR-120, Amberlite 200 from Rohm & Haas, Dowex M-31 from DOW, K 2611, K 2431 from Bayer. The ion exchange capacity of the resins when entirely in the $H^+$ form is typically between 1 and 2 mol, in particular from 1.5 to 1.9 mol, of $H^+$ per liter of moist resin (as obtained commercially).

In the process of the invention, preference is given to using macroporous resins, for example K 2431 from Bayer, Amberlyst 15 or Amberlyst 35 from Rohm & Haas. The pore volume is preferably from 30 to 60 ml/g, in particular from 40 to 50 ml/g (based on commercial moist resin).

The particle size of the resin is preferably between 500 µm and 1500 µm, in particular between 600 µm and 1000 µm.

The particle size distribution selected may be narrow or wide. For example, ion exchange resins having very uniform particle size (monodisperse resins) can be used.

It may be advantageous to use relatively large particles to reduce the pressure differential in reactors which are flowed through at high linear rates, and to use relatively small particles to achieve the optimum conversion in reactors which are flowed through at a low linear rate.

Optionally, the ion exchange resins can be used in the form of shaped bodies, for example cylinders, rings or spheres.

The acidic ion exchange resin is advantageously adjusted to an activity which does enable the oligomerization of isobutene but barely catalyzes the cooligomerization of isobutene with linear butenes, the oligomerization of the linear butenes or the isomerization of the linear butenes. Also, the heat evolution in the reactor is adjusted to a value which can be safely controlled from a technical point of view.

The desired catalyst activity can be adjusted with the aid of moderators. These materials are passed over the catalyst together with the reactant. Examples of useful moderators include water, alcohols such as tert-butyl alcohol (TBA), methanol, isononanol or ethanol or ethers such as tert-butyl methyl ether (MTBE), either as a pure substance or mixtures. Preference is therefore given to carrying out the oligomerization in stage a) in the presence of these moderators. In this connection, useful molar ratios have proven to be from 0.01 to 5 mol, preferably from 0.01 to 1 mol, in particular from 0.01 to 0.7 mol, of moderator per mole of isobutene.

In the process according to the invention, it is advantageous to use that alcohol which is used for etherifying isobutene in the second reaction step or the ether formed in the second reaction step as the moderator, for example methanol or MTBE.

Also used for oligomerization in the process according to the invention are solid sulfonated ion exchange resins which have the desired activity without the addition of moderators. These are in particular partly neutralized ion exchange resins in which from 1 to 60%, preferably from 1 to 30%, most preferably from 5 to 15%, of the acidic protons of the sulfonic acid groups have been exchanged for metal ions. Metal ions which can replace the protons include alkali metal, alkaline earth metal, transition metal ions (group 1-12 metal ions such as chromium, manganese, iron, cobalt, nickel, zinc ions) and aluminum ions, and also ions of the lanthanide group (rare earths). Preference for this purpose is given to using alkali metal ions, in particular sodium ions. It is also possible that the ion exchange resin is laden with two or more different metal ions.

For the preparation of the partially neutralized ion exchange resins, it is possible to apply different processes which are all described in the technical literature. When the ion exchange resin is in the $H^+$ form, protons can be exchanged for metal ions. When the resin is in the metal salt form, metal ions can be replaced by protons with the aid of acids. In principle, this ion exchange can be effected either in organic or aqueous suspension.

In a simple process, for example, the ion exchange resin in the $H^+$ form is slurried with sufficient liquid to result in a readily stirrable suspension. A solution which contains the desired ions is metered in. After completed ion exchange, the ion exchange resin which has been partially exchanged is washed and dried.

The amount of solvent for slurrying the ion exchange resin is typically from one to ten times the intrinsic volume of the ion exchange resin. For the preparation of the solution of the desired type of ion which is metered in, it is advisable to select a solvent which is miscible with the solvent in which the resin is suspended. It is advantageous to use the same solvent.

The ion exchange is preferably effected within the temperature range of from 10 to 100° C., more preferably from 20 to 40° C. The exchange is generally complete after 24 hours at the latest. After the ion exchange, the catalyst is separated from the solution, for example by decanting or filtering, and then optionally washed with a solvent. It is advantageous to use the same solvent in which the catalyst was suspended.

It is advantageous to dry the moist catalyst, firstly to make it easier to handle (more free-flowing) and secondly to keep the contamination of the product by the adhering solvent or its subsequent products low in the first days after the startup of the reactor. The drying can be effected under reduced pressure or in an inert gas stream, for example in a nitrogen stream. The drying temperatures are typically between 10 and 120° C.

A preferred route for preparing the catalysts used in the process according to the invention is the exchange of protons for metal ions in the aqueous phase, washing the partly exchanged ion exchange resin with water and subsequent drying.

The ions with which the resin is to be laden may be solutions of hydroxides, or salts of organic or inorganic acids. In the case of salts of polybasic acids, it is also possible to use acidic salts. It is likewise possible to use compounds with other organic radicals, for example alkoxides or acetylacetonates. Preferred sources of the metal ions are metal hydroxides and salts of inorganic acids. Very particular preference is given to the use of alkali metal hydroxides (e.g. sodium hydroxide), alkali metal halides (e.g. sodium chloride), alkali metal sulfates (e.g. sodium sulfate), alkali metal nitrates (e.g. sodium nitrate), alkaline earth metal hydroxides and alkaline earth metal nitrates.

Depending on the degree of exchange, ion type and resin, the above-described method can be used to prepare catalysts of different activity and selectivity.

A reactor in the process according to the invention may contain a mixture of ion exchange resins of different reactivity. It is equally possible that a reactor contains catalysts of different activity arranged in layers. When more than one reactor is used, the individual reactors may be charged with catalysts of the same or different activity.

For the industrial performance of the conversion of the isobutenic hydrocarbon mixtures, various variants are possible. The conversion may be carried out batchwise or preferably in continuous reactors which are typically used in solid/liquid contact reactions. When continuous flow reactors are used, a fixed bed is usually, but not exclusively, used. An example of a different concept to fixed bed reactors are reactors in which the ion exchanger is suspended in a liquid phase (cf. "Bayer process", Erdöl und Kohle, Erdgas, Petrochemie, 1974, 27, Volume 5, page 240).

When a fixed bed flow reactor is used, the liquid can flow upward or downward. Preference is usually given to the liquid flowing downward. A cooling liquid flowing around the reactor may optionally have the same or opposite flow direction. It is also possible to operate the reactor with product recycling or in straight pass.

When using tubular reactors, the ratio of length to diameter of the catalyst bed can be varied, either via the geometric dimensions of the reactor or via its fill level. At the same amount of catalyst and liquid hourly space velocity (LHSV), different superficial velocities can therefore be achieved.

The reactors used in the industrial process may be operated adiabatically, polytropically or virtually isothermally. Virtually isothermally means that the temperature at an arbitrary point in the reactor is a maximum of 10° C. higher than the temperature at the reactor entrance. In the case of adiabatic operation of the reactors, it is generally sensible to arrange a plurality of reactors in series and to cool between the reactors. Reactors which are suitable for polytropic or virtually isothermal operation are, for example, tube bundle reactors, stirred tanks and loop reactors.

It is possible to combine a plurality of reactors, also of different designs. It is additionally possible to operate reactors with recycling of product.

The temperatures at which the oligomerization is conducted are between 5 and 160° C., preferably between 40 and 110° C.

The conversion can be effected with and without addition of a suitable solvent. Preferred solvents are saturated hydrocarbons, in particular $C_4$, $C_8$ or $C_{12}$ hydrocarbons. Very particular preference is given to using isooctane. When solvents are added, their content is from 0 to 60% by weight, preferably from 0 to 30% by weight.

The conversion according to the invention can be carried out at a pressure equal to or greater than the vapor pressure of the starting hydrocarbon mixture at the particular reaction temperature, preferably at a pressure of less than 40 bar, i.e. the isobutenic hydrocarbon mixtures are entirely or partly in the liquid phase during the oligomerization. When the reaction is to be carried out entirely in the liquid phase, the pressure should be from 2 to 4 bar higher than the vapor pressure of the reaction mixture, in order to avoid evaporation problems in the reactors.

Even when the reaction is conducted at a pressure at which the reaction mixture is not entirely liquid (for example in a reactive distillation or in process variants similar to U.S. Pat. No. 5,003,124), the oligomerization in the process according to the invention takes place nonetheless in the liquid phase, i.e. over a "moist", i.e. liquid-wetted, catalyst.

The overall conversion of isobutene to oligomers can be adjusted via the amount and type of the catalyst used, the reaction conditions set and number of reactors. In the process according to the invention, from 50 to 95% of the isobutene contained in the reactant, in particular from 60 to 90%, is oligomerized.

The reaction mixture of the partial isobutenic oligomerization can be worked up in different ways. The mixture is either passed directly to the etherification or the butene oligomers are removed before etherification. The oligomers and any hydrocarbons having from 5 to 7 carbon atoms are advantageously removed by distillation.

The removed oligomer fraction contains mainly $C_8$ hydrocarbons. In addition to the diisobutene, this may also contain codimers and higher oligomers ($C_{12}$, $C_{16}$). This fraction can be separated in further distillation steps. For example, it is possible to remove a fraction of highly pure diisobutene, in order to use this separately, for example for chemical syntheses. For use as a fuel component for gasoline engines, it may be necessary to remove high-boiling components (boiling point preferably >220° C.).

It is also possible to fully or partly hydrogenate the butene oligomers, in particular the $C_8$-olefins. Methods for hydrogenating the products of oligomerization to the corresponding paraffins are sufficiently well known to those skilled in the art. Common methods for hydrogenating olefins are described, for example, in F. Asinger, "Chemie und Technologie der Monoolefine", Akademie Verlag, Berlin, 1957, page 626-628 or DE 197 19 833.

In a preferred embodiment, the hydrogenation is carried out in the liquid phase over a solid catalyst insoluble in the material to be hydrogenated. Preferred hydrogenation catalysts are supported catalysts which consist of an inorganic support and, as the active metal, contain platinum and/or palladium and/or nickel. The temperature at which the hydrogenation is carried out is preferably in the range from 10 to 250° C. and the pressure between 1 and 100 bar.

After the hydrogenation, further fractions can be obtained by distillative separation. It is possible to obtain fuel additives having definite properties from these and from the unhydrogenated fractions by blending. Some fractions can also be used as solvents.

The isobutene-depleted $C_4$ hydrocarbon mixture is converted in a second reaction step (stage b) in the process according to the invention, in which the remaining isobutene is removed by addition of alcohol to give the corresponding tertiary ether. If required, additional low-isobutene $C_4$ hydrocarbons (for example raffinate II, optionally bought in) may also be added to this $C_4$ hydrocarbon mixture. These streams may stem from other processes, for example a TBA synthesis or an isobutene removal by hydroisomerization/distillation (cf. EP 1 184 361).

The etherification of the isobutene is carried out as an acid-catalyzed reaction.

The alcohols used therefor are primary, secondary, mono- or polyhydric alcohols having from 1 to 5 carbon atoms, preferably methanol or ethanol.

In order to achieve virtually complete conversion of the remaining isobutene, the addition of the alcohol to the isobutene is carried out in the presence of an acidic catalyst in at least two reaction stages, of which the last reaction stage is carried out as a reactive distillation. In the prereactor(s), a reaction mixture of the low-isobutene $C_4$ stream and alcohol is prepared over an acidic catalyst and is in the vicinity of the thermodynamic equilibrium with regard to its isobutene, alcohol and tert-butyl ether concentration. For methanol/MTBE, for example, this is generally between 94 and 96% isobutene conversion. This mixture is fed into the reactive distillation column, where a further portion of the isobutene is converted to the ether.

The prereactor or prereactors in which the alcohol is reacted with the isobutene up to close to the thermodynamic equilibrium may be conventional fixed bed reactors (tube bundle reactors, circulation reactors) They may be operated with or without partial recycling, optionally with cooling of the recycle stream.

The reactors are typically operated at from 30 to 110° C. and from 5 to 50 $bar_{abs}$ (bara). Since the thermodynamic equilibrium between alcohol/isobutene and ether at low temperature lies substantially to the side of the ether, preference is given when using a plurality of prereactors to operate the first of the reactors at higher temperature (high reaction rate) than the following (utilization of equilibrium point).

The catalyst used both in the prereactor and in the reactive distillation column is a solid material which is soluble neither in the feedstock mixture nor in the product mixture and has acidic centers on its surface. The catalyst must not give off any acidic materials to the product mixture under the reaction conditions because this would lead to yield losses.

In the reactive distillation column, the catalyst is either integrated in the packing, for example KataMax® (EP 0 428 265), KataPak® (EP 0 396 650) or MultiPak® (utility model No. 298 07 007.3) or polymerized to shaped bodies (U.S. Pat. No. 5,244,929).

The rule for the activity of the catalysts is that they effect the addition of alcohol to isobutene under the reaction conditions but hardly effect the addition to linear butenes. They must also barely catalyze the oligomerization of linear butenes and dialkyl ether formation from two molecules of the alcohol used. With regard to a high yield of 1-butene, the activity for the attainment of equilibrium between the linear butenes should be low.

Examples of useful solid catalysts include zeolites, acid-activated bentonites and/or clay earths, sulfonated zirconium oxides, montmorillonites or acidic ion exchange resins.

A preferred group of acidic catalysts in the process according to the invention are solid ion exchange resins having sulfonic acid groups. Suitable ion exchange resins are, for example, those which are prepared by sulfonating phenol/aldehyde condensates or cooligomers of aromatic vinyl compounds. Examples of aromatic vinyl compounds for preparing the cooligomers are styrene, vinyltoluene, vinylnaphthalene, vinylethylbenzene, methylstyrene, vinylchlorobenzene, vinylxylene and divinylbenzene. In particular, the cooligomers which result from reaction of styrene with divinylbenzene are used as a precursor for the preparation of ion exchange resins having sulfonic acid groups. The resins can be prepared in a gellike, macroporous or spongelike form. Strongly acidic resins of the styrene-divinylbenzene type are sold, inter alia, under the following tradenames: Duolite C20, Duolite C26, Amberlyst A15, Amberlyst A35, Amberlite IR-120, Amberlite 200, Dowex 50, Lewatit SPC 118, Lewatit SPC 108, K2611, K2621, OC 1501.

The properties of these resins, in particular specific surface area, porosity, stability, swelling or shrinkage and exchange capacity, can be varied via the preparation process.

In the process according to the invention, the ion exchange resins can be used in their H form. Preference is given to using macroporous resins, for example Lewatit SCP 118, Lewatit SCP 108, Amberlyst A15 or Amberlyst A35, K2621. The pore volume is from 0.3 to 0.9 ml/g, in particular from 0.5 to 0.9 ml/g. The particle size of the resin is between 0.3 mm and 1.5 mm, in particular between 0.5 mm and 1.0 mm. The particle size distribution selected may be large or small. For example, ion exchange resins having very uniform particle size (monodisperse resins) can be used. The capacity of the ion exchanger, based on the commercial form, is 0.7-2.0 mol/l, in particular 1.1-2.0 mol/l.

The remaining isobutene is reacted with alcohol to give the corresponding tertiary butyl ether in the temperature range of 10-140° C. The alcohol is used in excess.

In particular, the remaining isobutene is removed by reaction with methanol to give MTBE. The procedure is in particular as described in DE 101 02 082. The low-isobutene $C_4$ hydrocarbon mixture is fed into the prereactor together with methanol. A mixture is formed there in which isobutene, methanol and MTBE are at equilibrium or virtually at equilibrium. This reaction mixture is passed into the reactive distillation column.

More methanol may be present in the feed of the reactive distillation column than is required for the complete conversion of the isobutene still present. However, the methanol excess should be limited in such a way that on the one hand there is a sufficient amount of methanol for the azeotrope of methanol and $C_4$ hydrocarbons which forms, but on the other hand not so much that methanol could get into the bottom product, so that on-spec MTBE (methanol content preferably below 5000 ppm by weight) is obtained. However, this only applies when the oligomers have been removed beforehand. Otherwise, a mixture of MTBE and oligomers is obtained.

When the methanol content in the column feed is below the maximum permissible value, additional methanol may optionally be added. In addition, methanol can be fed in at the top of the reactive distillation column via a separate apparatus.

In the reactive distillation column, the zone above the catalyst packing consists of from 5 to 20, in particular from 10 to 15, plates. The catalyst zone can be estimated as having a distillative action of from 1 to 5 theoretical plates per meter of packing height. The separating zone below the catalyst comprises from 12 to 36, in particular from 20 to 30, plates.

Irrespective of its composition, reaction pressure in the column and throughput, the temperature of the column feed is between 50° C. and 80° C., preferably between 60° C. and 75° C.

Depending on the pressure in the column, the average temperature in the catalyst zone is preferably from 55° C. to 70° C., more preferably from 58° C. to 67° C.

The reactive distillation column is operated at pressures, measured at the top of the column, of from 3 bara to 15 bara, preferably from 5 bara to 9 bara, in particular from 7 bara to 8.5 bara.

The hydraulic loading in the catalytic packing of the column is preferably from 10% to 110%, preferably from 20% to 70%, of its flood point loading. The hydraulic loading of a distillation column refers to the uniform flow demands on the column cross section by the rising vapor stream and the refluxing liquid stream. The upper loading limit indicates the maximum loading by vapor and reflux liquid above which the separating action falls as a consequence of entrainment or accumulation of the reflux liquid by the rising vapor stream. The lower loading limit indicates the minimum loading below which the separating action falls or collapses as a consequence of irregular flow or the column running empty, for example the trays. (Vauck/Müller, "Grundoperationen chemischer Verfahrenstechnik [Basic operations of chemical process technology], p. 626, VEB Deutscher Verlag für Grundstoffindustrie.)

At the flood point, the shear stresses transferred from the gas to the liquid are so great that the entire amount of liquid is entrained with the gas in the form of droplets, or that there is phase inversion in the column (J. Mackowiak, "Fluiddynamik von Kolonnen mit modernen Füllkörpern und Packungen für Gas/Flüssigkeitssysteme" [Fluid dynamics of columns having modern random packings and structured packings for gas/liquid systems], Otto Salle Verlag 1991).

The reactive distillation column is operated at reflux ratios of less than 1.5, in particular at those which are greater than 0.4 and less than 1, preferably between 0.5 and 0.9.

The optimum reflux ratio depends on the throughput of the composition of the column feed and on the column pressure. However, it is always within the abovementioned ranges. In the distillate of the reactive distillation, residual isobutene concentrations in the raffinate II (usual term for a mixture of $C_4$ hydrocarbons freed of 1,3-butadiene and isobutene) of less than 1000 ppm by weight, preferably 500 ppm by weight, most preferably less than 300 ppm by weight (based on the $C_4$ mixture in the distillate), are obtained.

When the butene oligomers are removed before the reaction with methanol, the bottom product of the reactive distillation column preferably consists of MTBE. It preferably contains less than 2500 ppm by weight of methyl sec-butyl ether and less than 2500 ppm by weight of $C_8$ hydrocarbons.

The top product of the reactive distillation column may in turn be separated into a $C_4$ hydrocarbon mixture and methanol, and the $C_4$ hydrocarbon mixture preferably contains less than 0.5 ppm by weight of MTBE and/or TBA.

The methanol may, for example, be removed by extraction with water. If traces of butadiene have not already been removed before the butene oligomerization, they can be removed from the raffinate II obtained in this way by selective hydrogenation (SHP). The $C_4$ hydrocarbon mixture obtained from the reactive distillation and optionally freed of methanol may be further separated distillatively. For this purpose, there are two preferred routes:

1. separation into a top fraction which comprises 1-butene and isobutane, and a bottom fraction which comprises n-butane, 2-butenes and any residual amounts of 1-butene. The isobutane can be removed from the top fraction in a further distillation so that highly pure 1-butene remains, or
2. removal of the isobutane and any further low boilers in a first distillation step, in which 1-butene, 2-butenes and n-butane remain in the bottoms. 1-Butene can be obtained as a low boiler from the bottom product in a further distillation.

When alcohols other than methanol are used for the etherification, the parameters of the reactive distillation change correspondingly.

The pure 1-butene prepared in this way contains less than 1000 ppm by weight of isobutene and is in demand as an intermediate. It is used, for example, as a comonomer in the preparation of polyethylene (LLDPE or HDPE) and also of ethylene-propylene copolymers. It also finds use as an alkylating agent and is the starting material for preparing butan-2-ol, butene oxide, valeraldehyde.

A further use of the virtually isobutene-free raffinate II prepared in accordance with the invention is the preparation of n-butene oligomers, in particular by the Octol process.

The hydrocarbons remaining after reaction or conversion of the linear butenes from the raffinate II may optionally be worked up by hydrogenation (CSP=complete saturation process) to give isobutane and n-butane.

The tert-butyl ether occurring as a bottom product in the reactive distillation may be used for various purposes. In addition to the use as a component for gasoline fuels, it finds use, for example, as a solvent. Dissociation of tert-butyl ether provides isobutene of high purity.

In addition to the use as a component in gasoline fuel, the MTBE obtained when methanol is used is, for example, used as a solvent. To obtain MTBE of high purity which is preferably used as a solvent, the bottom product of the reactive distillation obtained in the process may be further purified distillatively. This reduces the content of impurities present in small amounts (for example, methyl sec-butyl ether, $C_8$-HCs, TBA, alcohols).

The dissociation of MTBE to obtain isobutene is described, for example, in DE 100 200 943. The purity of the isobutene obtained is dependent, among other factors, on the proportion of methyl sec-butyl ether in the MTBE. Depending on the requirements, the MTBE used for the dissociation has therefore been prepurified to different degrees of intensiveness.

When the oligomers are not removed before the etherification, the bottom product obtained in the reactive distillation column contains MTBE and the oligomers. This mixture may be used as a fuel component as such or after hydrogenation of the olefinic double bonds. Optionally, this mixture may be fractionated. The individual fractions are then used as already described.

Figure 2:
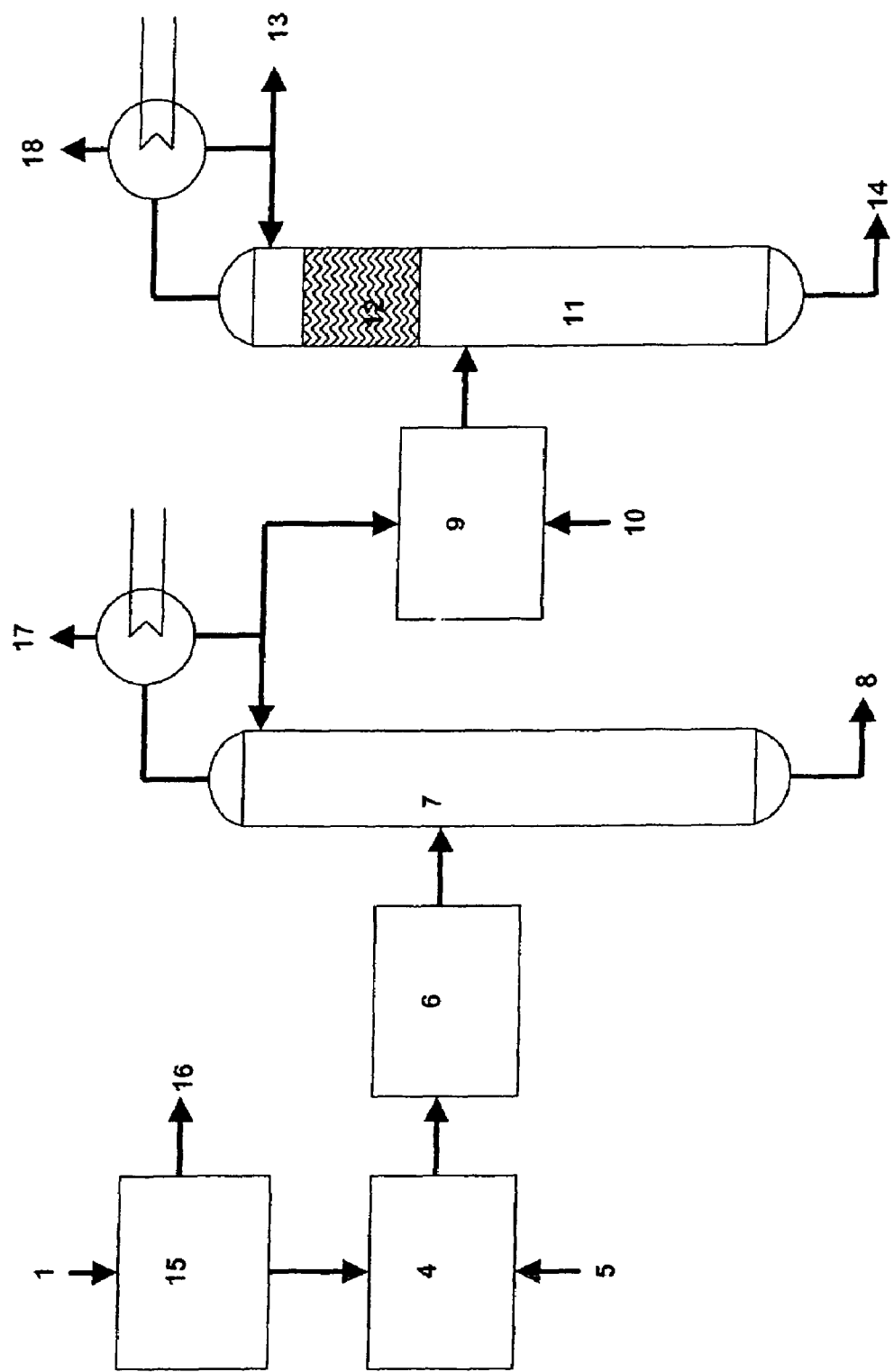
FIG. 2 shows a schematic diagram of an embodiment of the process of the invention.

Two embodiments of the process according to the invention are described in detail schematically with the aid of the figures, FIG. 1 and FIG. 2, without limiting the invention to these embodiments. In the schematic diagrams, only the essential stages are shown. For a better overview, the illustration of customary process streams, for example cooling water streams, circulation streams, catalyst recycle streams or recycle streams, and/or customary apparatus, for example heat exchangers or separators, has been dispensed with.

In the process illustrated schematically in FIG. 1, an isobutenic and 1,3-butadienic $C_4$ hydrocarbon 1 is fed into one or more reactors in which a butadiene hydrogenation is carried out, 2. Hydrogen 3 is also fed into this reactor for hydrogenation. The reactor effluent is transferred into a next reactor for selective residual butadiene hydrogenation 4, into which hydrogen is in turn fed 5. The reactor effluent from 4 is transferred to the reactor for butene oligomerization 6, in which the isobutene is mainly converted to dimers, trimers and tetramers. The effluent from this reactor is transferred to a distillation column 7 in which the butene oligomers are removed as the bottom product 8. The stream freed of butene oligomers is conducted via the top of the column 7 into a heat exchanger, in which the condensable constituents are condensed. These are partly recycled into the top of the column 7. In the heat exchanger, noncondensable constituents are fed to a further use as a gaseous offgas stream 17. The distillate of the column 7 is fed together with additional methanol 10 into the MTBE fixed bed stage 9, and the isobutene still present is reacted with it over the fixed bed catalyst to give MTBE. The effluent from the fixed bed stage is fed into a reactive distillation column 11 below the reactive packing 12. At the bottom of the column, a stream containing MTBE 14 is taken off, while the top product is conducted into a heat exchanger, in which the condensable constituents are condensed as an isobutene-free n-butene stream. These are partly recycled as reflux to the top of the column 11 and discharged from the process as stream 13. The fractions of the top product which cannot be condensed in the heat exchanger are fed to a further use as a gaseous offgas stream 18.

The process illustrated schematically in FIG. 2 differs from the process illustrated in FIG. 1 in that, instead of the butadiene hydrogenation 2, a butadiene removal 15, for example an extractive distillation, is carried out, which removes the majority of the 1,3-butadiene 16 from the isobutenic $C_4$ hydrocarbon stream 1. The butadiene-depleted stream from the butadiene removal 15 is subsequently transferred to a reactor for selective residual butadiene hydrogenation 4, and then further worked up as in FIG. 1.

The examples which follow are intended to illustrate the invention, without narrowing the scope of protection of the patent claims.

EXAMPLES

The individual process steps for the workup of a crack-$C_4$ stream ($CC_4$) were reproduced in the laboratory analogously to the process illustrated in FIG. 1.

Example 1

Selective Butadiene Hydrogenation

An HC mixture having the composition specified in Table 2 is hydrogenated in a fixed bed reactor over a heterogeneous palladium catalyst. In a similar manner to EP 0 523 482, the hydrogenation is carried out in two fixed bed reactors which are operated in series and are each equipped with a separator and a liquid circuit. In each of the liquid circuits is installed a cooler in order to be able to remove the heat of reaction of the hydrogenation.

The hydrogen required for the reaction was fed to the reactors in accordance with the amount of 1,3-butadiene to be converted. The LHSV over the entire plant was 8.5 t/(m³h).

Percentages of the analyses are to be interpreted as % by mass.

| Stage 1 | Reactor entrance temperature | 29° C. |
|---|---|---|
| | Pressure | 14 bara |
| | Catalyst | 0.5% Pd on $Al_2O_3$ |
| Stage 2 | Reactor entrance temperature | 45° C. |
| | Pressure | 9 bara |
| | Catalyst | 0.5% Pd on $Al_2O_3$ |

TABLE 2

Analyses of feed and effluent of the butadiene hydrogenation

| | Feed | Stage 1 effluent | Stage 2 effluent |
|---|---|---|---|
| C3—HC [%] | n.d., <0.1 | n.d., <0.1 | n.d., <0.1 |
| isobutane [%] | 2.3 | 2.3 | 2.3 |
| n-butane [%] | 5.5 | 5.9 | 6.3 |
| trans-butene [%] | 4.9 | 17.2 | 19.7 |
| 1-butene [%] | 15.9 | 37.1 | 40.4 |
| isobutene [%] | 24.8 | 24.8 | 24.8 |
| cis-butene [%] | 4.0 | 5.1 | 6.1 |
| 1,2-butadiene [%] | 0.2 | n.d., <0.1 | n.d., <0.1 |
| 1,3-butadiene [%] | 41.4 | 6.3 | 0.2 |
| butenyne [%] | 0.75 | n.d., <0.1 | n.d., <0.1 |
| 1-butyne [%] | 0.2 | n.d., <0.1 | n.d., <0.1 | n.d. = below the detection limit

Example 2

SHP, Further Reduction of the 1,3-butadiene Content

Residual amounts of 1,3-butadiene which are still present in the $C_4$ hydrocarbon mixture can be reduced in a further hydrogenation step. The addition of small amounts of carbon monoxide increases the selectivity of the palladium catalyst.

The experiment was carried out with two different raw materials. The feed specified under 2b corresponds to a composition as obtained from the process of Example 1 (hydrogenation of the 1,3-butadiene contained in the crack-$C_4$). The feed 2a represents a mixture of $C_4$ hydrocarbons which is obtained after removal of the 1,3-butadiene from the crack-$C_4$ (FIG. 2).

The HC mixtures having the composition specified in Table 3 are admixed with 85 ppm of hydrogen and 2 ppm of carbon monoxide. The hydrogenation was effected in a fixed bed reactor under the following conditions:

Temperature: 40° C. (isothermal)

Pressure: 13 bara

LHSV: 35 (l/(l*h))

Catalyst: 0.5% of Pd on γ-$Al_2O_3$ support

TABLE 3

Analysis of feed and effluent of the SHP (selective hydrogenation process)

| | Example | | | |
|---|---|---|---|---|
| | 2a feed | 2a effluent | 2b feed | 2b effluent |
| C3—HC [%] | 0.0 | 0.0 | <0.1 | <0.1 |
| isobutane [%] | 3.9 | 3.9 | 2.3 | 2.3 |
| n-butane [%] | 9.5 | 9.5 | 5.9 | 5.9 |
| trans-butene [%] | 8.5 | 8.6 | 17.6 | 17.6 |
| 1-butene [%] | 27.6 | 27.7 | 40.9 | 41.1 |
| isobutene [%] | 43.1 | 43.1 | 24.8 | 24.8 |
| cis-butene [%] | 6.9 | 6.9 | 8.2 | 8.2 |
| 1,2-butadiene [ppm] | <100 | n.d. | <1 | n.d. |
| 1,3-butadiene [ppm] | 2176 | 3 | 1960 | 2 |
| butenyne [ppm] | n.d. | n.d. | 12 | n.d. |
| 1-butyne [ppm] | n.d. | n.d. | 56 | n.d. | n.d. = below the detection limit

Example 3

Isobutene Oligomerization and Distillation

The isobutene was oligomerized in a tubular reactor of length 200 cm (wound to a spiral), internal diameter 6 mm. The tube is heated externally by an oil bath. The catalyst used was 54 ml of Amberlyst 15 from Rohm & Haas. Before use, the catalyst was washed with water, then with methanol. The reactor was operated at a constant 22 bara using a pressure regulator at the reactor exit. After startup, the experimental plant was operated for 24 hours and the product was discarded. Afterwards, the product of the plant was collected over 100 hours and distilled in a laboratory column. The fractions obtained were analyzed by gas chromatography. Table 4 lists the process conditions, reactant compositions and the analyses of the $C_4$ and the $C_8$ fraction. In the table, Isobutene conversion: proportion of isobutene which was converted in the reactor.

$C_8$ selectivity: selectivity at which $C_8$ hydrocarbons (dimers of the butenes) were formed in the reaction.

The value quoted for 2,4,4-trimethylpentene under $C_8$ analysis states the proportion (percentage by mass) of the dimers of isobutene in the $C_8$ fraction.

Two experiments (3a, 3b) were carried out with feeds of different composition. In each experiment, fresh catalyst was used.

TABLE 4

Reaction conditions and analysis of the isobutene oligomerization

|  |  | Experiment No. | |
|---|---|---|---|
|  |  | 3a | 3b |
| Heating bath temp. | (° C.) | 62.5 | 62.5 |
| Reactor feed | (kg/h) | 0.300 | 0.306 |
| Feed analysis |  |  |  |
| propene | (%) | 0.01 | 0.00 |
| isobutane | (%) | 2.22 | 2.07 |
| n-butane | (%) | 10.32 | 9.20 |
| trans-butene | (%) | 25.83 | 9.21 |
| 1-butene | (%) | 2.92 | 27.10 |
| isobutene | (%) | 45.84 | 46.12 |
| cis-butene | (%) | 12.67 | 5.825 |
| remainder | (%) | 0.20 | 0.48 |
| Effluent analysis, C4 fraction (normalized to 100% of C4) | | | |
| isobutane | (%) | 4.16 | 3.74 |
| n-butane | (%) | 17.41 | 15.77 |
| trans-butene | (%) | 42.41 | 16.84 |
| 1-butene | (%) | 4.84 | 42.67 |
| isobutene | (%) | 11.71 | 9.75 |
| cis-butene | (%) | 19.21 | 10.66 |
| remainder | (%) | 0.25 | 0.58 |
| Isobutene conversion | (%) | 84.33 | 87.38 |
| C8 selectivity | (%) | 77.82 | 77.91 |
| Analysis of the C8 fraction (normalized to 100% of C8) | | | |
| 2,4,4-tri-Me-pentene | (%) | 91.40 | 92.60 |

Example 4

Isobutene Oligomerization Over Semi-Neutralized Ion Exchanger a) Preparation of a Semineutralized Catalyst, Adjustment of the Acid Capacity The Amberlyst 15 ion exchanger from Rohm and Haas used had an original acid capacity of 1.7 mol of $H^+$/l. To adjust the activity to that desired, 40% of the acidic centers were neutralized.

For this purpose, 1000 ml of the ion exchange resin were slurried in 1000 ml of deionized water and a solution of 27.2 g of sodium hydroxide (0.68 mol) and 500 ml of deionized water were added dropwise with stirring in the temperature range from 20 to 40° C. within one hour. Stirring was continued for 5 min and the ion exchange resin was then washed to neutrality with three times 1000 ml of deionized water. The subsequent capacity measurement of the partly neutralized ion exchanger gave 1.00 +/−0.03 mol of $H^+$/l. The catalyst was dried at 70° C. for 15 h before use.

b) Oligomerization

The isobutene was oligomerized in a similar manner to Example 3. 51 ml of the semineutralized ion exchanger were used. The reactor was operated at 22 bara. After an activation phase of 24 hours, the effluent of the reactor was analyzed by gas chromatography. Table 5 lists the process conditions, reactant compositions and the analysis, separated into the $C_4$ and the $C_8$ fraction.

Two experiments (4a, 4b) were carried out using feeds of different composition. In each experiment, fresh catalyst was used.

TABLE 5

Reaction conditions and analysis of the isobutene oligomerization

|  |  | Experiment No. | |
|---|---|---|---|
|  |  | 4a | 4b |
| Heating bath temp. | (° C.) | 100 | 100 |
| Reactor feed | (kg/h) | 0.509 | 0.480 |
| Feed analysis |  |  |  |
| propene | (%) | 0.00 | 0.00 |
| isobutane | (%) | 2.75 | 0.04 |
| n-butane | (%) | 8.52 | 13.85 |
| trans-butene | (%) | 8.98 | 17.23 |
| 1-butene | (%) | 29.00 | 19.17 |
| isobutene | (%) | 44.40 | 40.00 |
| cis-butene | (%) | 5.76 | 9.37 |
| remainder | (%) | 0.60 | 0.35 |
| Effluent analysis, C4 fraction (normalized to 100% of C4) | | | |
| isobutane | (%) | 3.41 | 0.06 |
| n-butane | (%) | 10.80 | 20.17 |
| trans-butene | (%) | 12.31 | 26.33 |
| 1-butene | (%) | 34.07 | 24.15 |
| isobutene | (%) | 30.45 | 14.18 |
| cis-butene | (%) | 8.37 | 14.77 |
| remainder | (%) | 0.60 | 0.35 |
| Isobutene conversion | (%) | 45.16 | 75.22 |
| C8 selectivity | (%) | 87.71 | 78.01 |
| Analysis of the C8 fraction (normalized to 100% of C8) | | | |
| 2,4,4-tri-Me-pentene | (%) | 94.48 | 90.53 |

Example 5

MTBE Synthesis in Fixed Bed Reactors

For the experiments, a construction similar to the isobutene oligomerization was used. The reactor consisted of a tube wound into a spiral which was heated externally by an oil bath. The front portion (approx. the first quarter) of the reactor was not charged with catalyst, in order to preheat the feed to the desired temperature. In experiment 5a, the back portion was charged with 125 ml of ion exchanger, and in experiment 5b with 94 ml of ion exchanger. The reactor was heated isothermally by the oil bath to 50° C.

The catalyst used was Amberlyst 15. The pressure of the plant was 8 bara.

The feed used was the $C_4$ fractions from Example 3. Analyses and feed amounts are specified in Table 6. Percentages are to be interpreted as % by mass.

TABLE 6

Feeds and analyses of the MTBE fixed bed experiments

|  |  | Experiment 5a | | Experiment 5b | |
|---|---|---|---|---|---|
| C4 feed | (g/h) | 100 | | 100 | |
| methanol feed | (g/h) | 7.7 | | 6.4 | |
|  |  | Feed analysis | Effluent analysis | Feed analysis | Effluent analysis |
| methanol | (%) | 7.15 | 1.26 | 6.03 | 1.11 |
| isobutene | (%) | 10.87 | 0.57 | 9.15 | 0.57 |
| MTBE | (%) | 0.00 | 16.19 | 0.00 | 13.50 |
| n-butane | (%) | 16.19 | 16.17 | 14.81 | 14.82 |
| isobutane | (%) | 3.84 | 3.86 | 3.52 | 3.51 |
| 1-butene | (%) | 4.48 | 4.49 | 40.07 | 40.10 |
| cis-butene | (%) | 17.84 | 17.84 | 10.04 | 10.02 |
| trans-butene | (%) | 39.38 | 39.39 | 15.82 | 15.83 |
| remainder | (%) | 0.24 | 0.23 | 0.56 | 0.55 |

Example 6a

Reactive Distillation

The schematic construction of the reactive distillation column is reproduced in FIGS. 1 and 2. The diameter of the column was 312.7 mm. In the upper portion of the column, approx. 2 m of Montz-Pak A3-500 were installed as a rectifying section. Below this, likewise in the rectifying section of the column, were disposed approx. 11.4 m of Katapak-SP 12. The lower section of the column consisted of approx. 3.6 m of Montz-Pak A3-500.

The feed position was disposed in the upper third of the lower Montz-Pak A3-500.

The catalyst used in the Katapak-SP 12 was Amberlyst 15. The pressure of the apparatus was 7.5 bara.

The feed for the column was a mixture made up of product streams of an industrial scale plant. The isobutene, MTBE and methanol concentrations were set substantially identically to those of the effluents of the laboratory reactors from Example 5. The composition of the remaining $C_4$ hydrocarbons is comparable to the effluents of the laboratory reactors from Example 5.

The feed rate was 700 kg/h. A reflux ratio of 1.09 was set. 578.8 kg/h of distillate and 121.2 kg/h of bottom product were obtained. Percentages are to be interpreted as % by mass.

The isobutene content measured in the distillate was 136 ppm.

| Experiment 6a | | Feed analysis | Distillate analysis | Bottoms analysis |
|---|---|---|---|---|
| methanol | (%) | 1.26 | 1.14 | 0.00 |
| isobutene | (%) | 0.57 | 0.01 | 0.00 |
| MTBE | (%) | 16.19 | 0.00 | 95.82 |
| n-butane | (%) | 14.17 | 17.24 | 0.01 |
| isobutane | (%) | 4.995 | 6.08 | 0.00 |
| 1-butene | (%) | 7.855 | 9.57 | 0.00 |
| cis-butene | (%) | 16.84 | 20.49 | 0.03 |
| trans-butene | (%) | 37.39 | 45.48 | 0.03 |
| remainder | (%) | 0.73 | 0.00 | 4.11 |

Example 6b

Reactive Distillation

In the same reactive distillation plant as described in Example 6a, an experiment was carried out with a reactant stream of different composition.

The catalyst used was likewise Amberlyst 15. The pressure of the apparatus was 7.5 bara.

The feed rate was 700 kg/h. A reflux ratio of 1.09 was set. 595.5 kg/h of distillate and 104.5 kg/h of bottom product were obtained. Percentages are to be interpreted as % by mass.

An isobutene content in the distillate of 102 ppm was measured.

| Experiment 6b | | Feed analysis | Distillate analysis | Bottoms analysis |
|---|---|---|---|---|
| methanol | (%) | 1.11 | 0.93 | 0.00 |
| isobutene | (%) | 0.57 | 0.01 | 0.00 |
| MTBE | (%) | 13.50 | 0.00 | 96.28 |
| n-butane | (%) | 12.84 | 15.09 | 0.01 |
| isobutane | (%) | 5.49 | 6.46 | 0.00 |
| 1-butene | (%) | 36.77 | 43.23 | 0.01 |
| cis-butene | (%) | 11.13 | 13.07 | 0.03 |
| trans-butene | (%) | 18.05 | 21.21 | 0.02 |
| remainder | (%) | 0.55 | 0.00 | 3.65 |

The reference numerals in FIG. 1 and FIG. 2 have the following meanings:
1. Isobutenic $C_4$ hydrocarbon stream
2. Butadiene hydrogenation
3. Hydrogen
4. Selective residual butadiene hydrogenation
5. Hydrogen
6. Butene oligomerization
7. Distillation for oligomer removal
8. Butene oligomers
9. MTBE fixed bed stage
10. Methanol
11. Reactive distillation column
12. Reactive packing of the reactive distillation column
13. Isobutene-free n-butene stream
14. MTBE
15. Butadiene extraction
16. Butadiene
17. Offgas stream
18. Offgas stream

What is claimed is:

1. A process for coproducing butene oligomers and tert-butyl ethers from isobutenic $C_4$ streams by
    a) partly oligomerizing the isobutenic $C_4$ streams over an acidic catalyst to give butene oligomers, and subsequently
    b) etherifying the remaining isobutene with an alcohol under acidic catalysis to give tert-butyl ethers,
    wherein
    the etherification is carried out under acid catalysis in stage b) in at least two reaction stages, of which at least the last reaction stage is carried out as a reactive distillation, and the butene oligomers obtained in stage a) are removed before the acid-catalyzed etherification in stage b).

2. The process as claimed in claim 1,
    wherein
    the acidic catalyst used in stage a) is an ion exchanger whose protons have partly been exchanged for metal ions of groups 1 to 12 of the Periodic Table.

3. The process as claimed in claim 2,
wherein
from 1 to 60% of the protons of the ion exchanger used in stage a) have been exchanged for metal ions.

4. The process as claimed in claim 1,
wherein
the oligomerization in stage a) is carried out up to an isobutene conversion of from 50 to 95%.

5. The process as claimed in claim 1,
wherein
the oligomerization in stage a) is carried out in the presence of a moderator.

6. The process as claimed in claim 5,
wherein
the moderator used is MTBE, TBA, methanol or water in a molar ratio of from 0.01 to 5 per mole of isobutene.

7. The process as claimed in claim 1,
wherein
the alcohol used in stage b) is methanol or ethanol.

8. The process as claimed in claim 1,
wherein
the polyunsaturated hydrocarbons contained in the isobutenic $C_4$ streams are catalytically hydrogenated before the oligomerization in stage a).

9. The process as claimed in claim 8,
wherein
the polyunsaturated compounds are hydrogenated in at least two reaction stages, of which at least the last reaction stage is carried out in the presence of 0.05-100 ppm by weight of CO.

10. The process as claimed in claim 1,
wherein
more than 90% of the butene oligomers obtained in stage a) are isobutene oligomers.

* * * * *